Dec. 12, 1972 W. H. COLLINS Plant Pat. 3,267

FLOWERING CRABAPPLE TREE

Filed Feb. 8, 1971

INVENTOR
WILLIAM H. COLLINS

Oberlin, Maky, Donnelly & Renner
ATTORNEYS

United States Patent Office

Plant Pat. 3,267

Patented Dec. 12, 1972

3,267

FLOWERING CRABAPPLE TREE

William H. Collins, Circleville, Ohio, assignor to Cole Nursery Company, Inc., Circleville, Ohio Filed Feb. 8, 1971, Ser. No. 113,774
Int. Cl. A01h 5/03
U.S. Cl. Plt.—34 1 Claim The present invention or discovery relates to a new and distinct variety of ornamental crabapple tree originated by me, having in combination novel fruit, foliage, and habit of growth, and more particularly consists in a novel variety of Malus, flowering crabapple, having unusual and distinctive characteristics.

My new flowering crabapple tree is a small tree of medium growth rate having upright spreading branches and unusually attractive foliage. It regularly bears an abundance of small glossy bright to dark red fruits which persist for an extended period of time.

The principal novel and distinctive features of this new variety are accordingly considered to be, in combination:

(1) An abundance of very firm, small, glossy, bright to dark red fruits whose color and firmness persist into the new year with minimal shriveling or shrinking and with the continuance of a high degree of gloss to the fruit surface.

(2) The relatively large leathery dark green leaves having excellent resistance to leaf diseases which generally persist until freezing temperatures occur.

(3) The superior structural form, including a straight, sturdy trunk and stiff, well spaced, well arranged branches that diverge from the trunk at wide angles.

(4) Trunk bark color on younger trees a pleasing medium brown color, carrying a slight sheen.

There is a large demand for small ornamental flowering trees for landscape planting, and flowering crabapple trees have been recognized over a long period of time as especially suitable for such purposes. The tree of the present invention is particularly desirable because it affords, in combination, handsome foliage, attractive flowers during the blooming period, and an abundance of glossy bright to dark red fruits which persist for a long period of time after leaf drop. The ornamental character of the tree is accordingly maintained over an exceptionally long portion of the year.

My new flowering crabapple tree is hardy at Painesville, Ohio, and has been propagated asexually at Circleville, Ohio, by budding and grafting, and the tree can be very readily propagated in this manner, perpetuating all of its original characteristics. The original parent specimen was a seedling grown by me at Painesville, Ohio, and such original parent specimen was discovered and selected by me in a large plantation of crabapple tree seedlings in 1961.

Referring now more particularly to the drawing.

Figure 1:
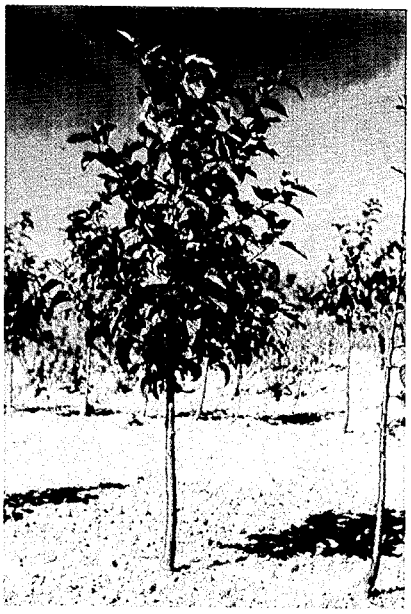
FIG. 1 shows my new flowering crabapple tree in foliage.
Figure 2:
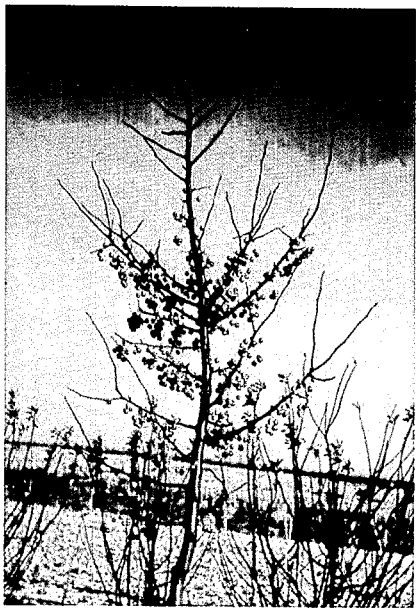
FIG. 2 shows my new flowering crabapple tree after foliage drop in the fall.
Figure 3:
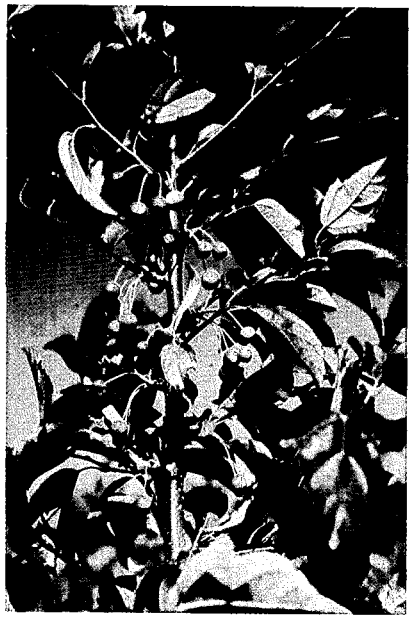
FIG. 3 shows the fruit of my new flowering crabapple tree produced during the period of foliage retention.
Figure 4:
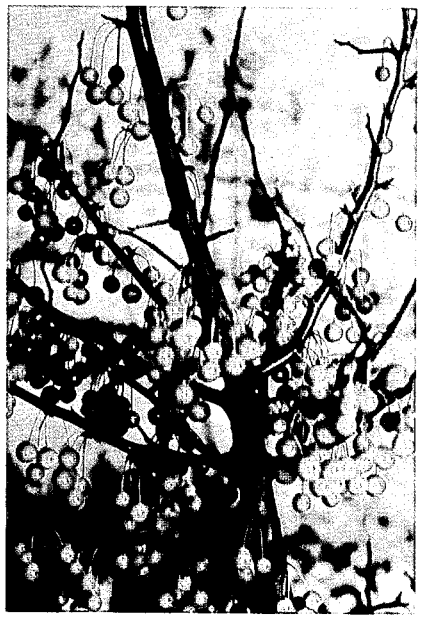
FIG. 4 is a late fall view of my new flowering crabapple tree showing the persistent character and glossy color of the fruit.

The following is a specific description of such new variety, the color terminology being based on the Nickerson Color Fan approved by the American Horticultural Society.

The original specimen is a tree about 14 feet in height, and the trees first propagated therefrom are about 10–12 feet in height. They would be classified as of medium growth rate with upright spreading branches and the main trunk is very straight and stiff, making an excellent shaped tree of relatively compact habit of growth. The side branches diverge upwardly with strong crotches. The twigs are prominently lenticulate, moderate reddish brown (7.5R 3/6 to 2.5YR 3/3) and glossy on the younger twigs to olive green (7.5Y 4/3 to 2.5GY 4/3) on the older twigs. The twigs are glabrous except at the tips where they become slightly hairy. The side buds are ovid, 3–5 mm. long, scaly, slightly pubescent and somewhat ciliate. The buds are brown with gray pubescenses and adhere closely to the stem.

The leaves are very attractive, of firm texture, strong green (5G 4/7) to moderate olive green (7.5GY 4/4) and glossy on the upper side. They are lighter green beneath. Leaves on fruiting branches are elliptical, mostly serrate or crenate; the blade is mostly 6.5–9.0 cm. long and 2.0–4.0 cm. wide. Occasionally, leaves have a lobe on one side, or are 3-lobed. Leaves on strong vegetative shoots are strongly 3-lobed, mostly 7.0–9.0 cm. long and 6.0–7.0 cm. wide. The lobes are shallowly serrate. There are 5–6 pairs of anastomosing veins, reddish on the underside. The leaves are essentially glabrous above or slightly hairy on the midrib on vigorous shoots, being mostly glabrous beneath except on the veins. The tip of the leaf is acute to short acuminate, the base variable, cuneate to rounded to slightly cordate. Stipules are present and leafy, to 15–16 mm. on vigorous shoots, but less prominent on fruiting branches. The petioles are mostly 1.5–2.5 cm. long, those on fruiting branches being longer and quite slender, while those on vegetative shoots are shorter, heavier and quite grooved. The leaves are held late in the season, ½ to ⅔ of the leaves remaining on the tree on Nov. 11, 1969, at Painesville, Ohio.

The flowers are borne medium abundantly, 5–10 per cluster, and are well distributed on the branches. They are displayed prominently on stiff, long pedicels, 3–4 cm. long. In bud, they are very pale pink (2.5R 9/3 or lighter, and moderately attractive. The open flowers are single, essentially white or with a very faint blush, and small, being 2.5–3.2 cm. across, and occasionally failing to open perfectly. There are usually 5 petals, 1.1–1.6 cm. long, with a short claw. The peak flowering period at Painesville, Ohio, is about May 8–14.

The fruits are small, glossy, 0.8–1.3 cm. broad and long, subglobosed to nearly rounded, and sometimes slightly ribbed, being borne 2–8 and usually 4–5 per cluster on short spurs. The final color is mostly strong red (5R 4/12) to dark red (5R 3/7), coloring somewhat unevenly from greenish yellow, depending upon exposure. The peak color is a strong or bright cherry red (2.5R 5/12 to 2.5R 4/10). The calyx is deciduous, and the calyx end is slightly depressed with quite a prominent scar. The stem end is slightly depressed. The bright purplish red fruit stems are 3.2–4.0 cm. long, slender, and with the fruit drooping and very firmly attached to the stem spur. The fruit itself is very firm, holding both its glossiness and its firmness to mid December with no fruit drop. The fruit shrivels only slightly after freezing weather and does not become soft and mushy. While the fruit color continues to darken, a degree of glossiness persists into February or March.

Because of its excellent growth habit, attractive foliage, and beautiful fruit this cultivar will prove very useful for general landscape, street, mall, park and other municipal area planting.

I claim:

1. A new and distinct variety of flowering crabapple tree, *Malus cultivar,* having an abundance of small, glossy, bright to dark red fruits, well distributed and displayed on the upper two-thirds of the plant that persist in a firm and attractive condition after leaf drop and well into late fall or early winter or later, with such glossiness persisting even after the fruits start to shrivel; relatively large, leathery, dark green, glossy foliage that holds late; and a sturdy, straight trunk, the stiff scaffold branches diverging at wide or nearly wide angles to the trunk assuring strong crotch structure, resulting in a small tree of sturdy upright compact branching habit.

No references cited.

ROBERT E. BAGWILL, Primary Examiner